United States Patent [19]

Highe et al.

[11] Patent Number: 5,345,934
[45] Date of Patent: Sep. 13, 1994

[54] ELECTRODE CONSTRUCTION AND PACKAGE THEREFOR AND METHOD

[75] Inventors: Albert J. Highe, Redwood City; Mir A. Imran, Palo Alto, both of Calif.

[73] Assignee: Physiometrix, Inc., Sunnyvale, Calif.

[21] Appl. No.: 983,824

[22] Filed: Dec. 1, 1992

Related U.S. Application Data

[63] Continuation-in-part of Ser. No. 790,412, Nov. 8, 1991, abandoned.

[51] Int. Cl.$^5$ .............................................. A61B 5/04
[52] U.S. Cl. .................................................. 128/639
[58] Field of Search ............... 128/639, 640; 607/152, 607/115

[56] References Cited

U.S. PATENT DOCUMENTS

| | | | |
|---|---|---|---|
| 4,226,247 | 10/1980 | Hauser et al. | 128/641 |
| 4,524,087 | 6/1985 | Engel | 128/639 |
| 4,706,679 | 11/1987 | Schmidt et al. | 128/639 |
| 4,781,798 | 11/1988 | Gough | 128/639 |

FOREIGN PATENT DOCUMENTS

WO8402423 6/1980 PCT Int'l Appl.

*Primary Examiner*—William E. Kamm
*Assistant Examiner*—Scott M. Getzow
*Attorney, Agent, or Firm*—Flehr, Hohbach, Test, Albritton & Herbert

[57] ABSTRACT

Electrode construction having a support structure. A conductive material is carried by the support structure. The conductive material has a length which is at least as great as its width.

18 Claims, 1 Drawing Sheet

ELECTRODE CONSTRUCTION AND PACKAGE THEREFOR AND METHOD

This application is a continuation-in-part of application Ser. No. 07/790,412 filed on Nov. 8, 1991 now abandoned.

This invention relates to an electrode construction and package therefor which is particularly useful in making EEG measurements.

Electrodes heretofore utilized for making EEG measurements typically have been of high impedance and have sought to make good contact with the skin of the patient. This has involved the use of electrodes whose are of contact is not well controlled which are based upon hydrogel kinds of materials. Such electrodes formed of hydrogel have a tendency to lose water and therefore are inappropriate for long term monitoring. Also for this reason they have a short shelf life. In addition, with respect to prior art electrodes, there has been an inability to compensate for the varying thicknesses of hair on the head of a patient when making measurements on the head. In addition, prior art electrodes typically must be prepared prior to use. Preparation of such electrodes requires considerable time and results in electrodes whose potentials which have not stabilized before use resulting in increased noise in EEG signals. There is therefore a need for a new and improved electrode construction which overcomes these disadvantages.

In general, it is the object of the present invention to provide an electrode construction which is particularly useful in making EEG measurements.

Another object of the invention is to provide an electrode construction which can utilize gel electrolytes as well as dry-type electrode materials.

Another object of the invention is to provide an electrode construction of the above character which can be used for long term monitoring and which has a relatively long shelf life.

Another object of the invention is to provide packaging and a method for the electrode construction of the present invention which provides electrochemically stable electrodes that are matched and do not require further conditioning before use.

Additional objects and features of the invention will appear from the following description in which the preferred embodiments are set forth in detail in conjunction with the accompanying drawings.

In general, the electrode construction of the present invention consists of a support structure. A conductive material is carried by the support structure and has a length and a width. The conductive material has an aspect ratio in which the length is at least as great as the width.

Figure 1:
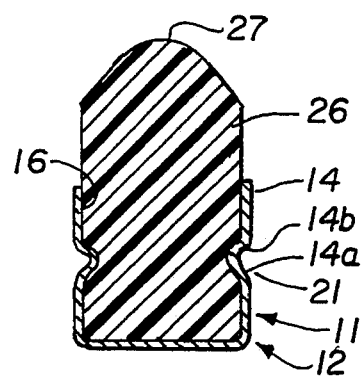
FIG. 1 is a side elevational view in cross-section of an electrode construction incorporating the present invention utilizing a dry-type conductive material.

More in particular, as shown in FIG. 1 of the drawings, the electrode construction 11 consists of a support structure in the form of a casing 12 which is formed of a conductive material. The casing 12 need not be highly conductive because it is only necessary to pass a small amount of current. Thus, it can be formed of a metal such as brass. It also can be formed of a conductive plastic or a metallized plastic. The casing 12 is shown as being generally cylindrical in shape and can be formed as a single piece deep-drawn casing. The casing 12 is provided with a circular top wall and a cylindrical sidewall 14 adjoining the top wall which defines a cylindrical recess 16 therein.

An annular recess 21 is formed in the casing 12 is adapted to be engaged by spring fingers (not shown) of the type disclosed in the co-pending application Ser. No. 07/790,412 filed on Nov. 8, 1991. The recess 21 is provided with an upwardly and inwardly inclined portion 14a as viewed in FIG. 1, and an upwardly and outwardly inclined portion 14b as shown in FIG. 1.

A conductive electrode material 26 is disposed within the recess 16 in the casing 12. The conductive material 26 can be of a self-supporting, dry-like material such as that disclosed in co-pending application Ser. No. 07/582,749 filed on Sep. 14, 1992. As described therein, that material can be in the form of a conductive elastomer which has silver-coated glass particles disposed therein. The conductive material 26 as shown in FIG. 1 is generally cylindrical in shape and extends beyond the casing 12 and has a rounded tip 27. The electrode construction 11 has an aspect ratio in which the length is at least as great as the width and as shown, has a length which is approximately the same as its width. By way of example, an electrode constructed in accordance with the present invention had a diameter of 0.3" and had a length of 0.5".

The surface forming the rounded tip 27 can be coated with a material which helps to impart electrochemical stability to the electrode material. For example, the surface of the tip which has silver-coated particles therein can be treated to form a silver silver chloride (AgCl) coating to impart electrochemical stability and to provide a reference potential. This coating can be applied by usual application. Preferably it is applied electrochemically by immersing the tip in a chloride-containing electrolyte bath and passing a small d.c. current i.e. one milliamp for approximately one minute through the electrode material with the negative voltage applied to a counter electrode in the electrolyte and the positive voltage applied to the support structure. The surface of the tip also can be coated with a hydrogel-type material to help bridge to and pre-wet the surface of the skin of the patient when making contact with the skin of the patient.

Figure 2:
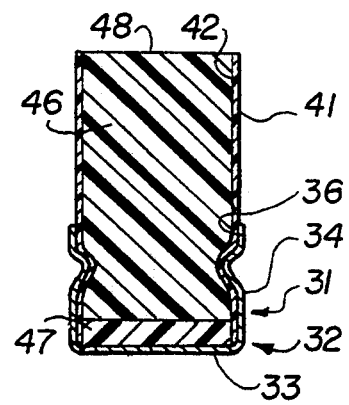
FIG. 2 is a cross-sectional view similar to FIG. 1 of another embodiment of an electrode construction incorporating the present invention utilizing a gelled electrolyte.

Another embodiment of an electrode construction incorporating the present invention is shown in the electrode construction 31 shown in FIG. 2. It consists of a support structure in the form of a cylindrical casing 32 which has a top wall 33 and a sidewall 34 with a cylindrical recess 36 therein. It is also provided with an annular recess 38 in the sidewall 34 which has generally the same conformation as the annular recess 21. A cylindrical sleeve 41 is secured to the casing 32 by suitable means as such an adhesive (not shown). The sleeve 41 is provided with a bore 42 which opens into the cylindrical recess 36 in the casing 32. The sleeve 41 can be formed of a suitable material such as plastic. The sleeve 41 can have a wall thickness ranging from a mil up to 1/16″. However, it should be fairly compliant so that when placed in contact with the skin of a patient it will have some "give."

The sleeve 41 should be formed of a material which substantially slows the rate of water loss and preferably is impervious to moisture and therefore serves as a moisture barrier membrane. This moisture barrier characteristic can also be achieved by applying a thin coating to the exterior of the sleeve 41. A conductive material 46 is provided within the bore 42 and extends into the cylindrical recess 36. The conductive material 46 is in contact with a coupling layer in contact with the wall 33 which provides a reference potential. It is formed of a suitable materials such as silver chloride (AgCl) deposited onto silver metal. This coating can be applied by normal application. Preferably it is applied electrochemically when the gelled electrolyte contains the coating. Preferably it is applied immersing the tip in an electrolyte or placing the tip against a suitable counter electrode and passing a small d.c. current i.e. one milliamp for approximately one minute through the electrode material with the negative voltage applied to the counter electrode and the positive voltage applied to the support structure. The conductive material 46 is provided for example, in the form of a gelled electrolyte and is retained within the sleeve 41 and provides a soft outer end 48 which can be flush with the end of the sleeve 41. It also can extend beyond the end of the sleeve. The gelled electrolyte can be rendered conductive by adding salts such as potassium chloride or sodium chloride. The gelled electrolyte can be very soft, elastomeric and tacky. The gelled electrolyte should have a cohesive strength which is greater than its adhesive strength so that when it touches the skin, it adheres to the skin but when pulled away from the skin does not fracture. In other words it will stay substantially intact. This is aided by the fact that the gelled electrolyte is retained within the sleeve 41 and adheres to the sleeve 41. It should be able to accommodate elongation, as for example have an ultimate elongation of at least 50% and preferably greater than 100%.

The material should be relatively soft and conformable having a core penetration value ranging from about 50 to about 475 ($10^{-1}$ millimeters) and preferably 50 to 300 ($10^{-1}$ millimeters) as measured by ASTM D217-88.

The conductivity of the conductive material utilized in the embodiments of the electrode construction shown in FIGS. 1 and 2 should have a conductivity at one KHz of less than 5,000 ohm-cm and preferably should have a conductivity of less than 1,000 ohm-cm.

Figure 3:
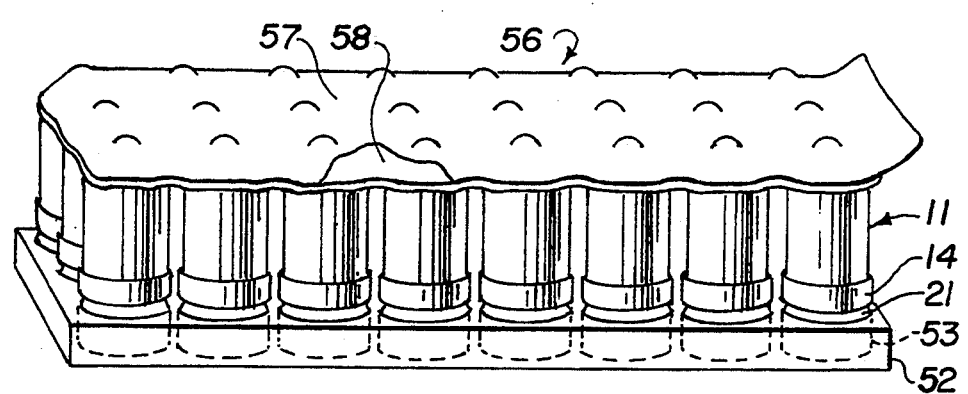
FIG. 3 is an isometric view of a package for the electrode construction shown in FIG. 2.

In the use of a conventional EEG procedure, it is typical to utilize as many as 19 electrodes in connection with a EEG headpiece of the type disclosed in co-pending application Ser. No. 07/790,412 filed on Nov. 8, 1991. Therefore, it is desirable to package at least that number in a single package or holder to minimize the differences in the reference potentials of the packaged electrodes and to stabilize the reference potentials of the electrodes. Thus, as shown in FIG. 3, there is shown holding means in the form of a holder or package 51 in which a plurality of 24 electrode constructions 11 of the type hereinbefore described are mounted therein. The holding means consists of a tray 52 which can be formed of a suitable material such as metal or a plastic coated with metal which has a plurality of holes 53 therein as for example a total of 24 holes arranged 3×8 as shown in FIG. 3. An arrangement such as 4×6 or 5×5 can be utilized if desired. The holes 53 are sized so that they can receive the casings 12 of the electrode construction 11 with the rounded ends 27 facing upwardly as shown in FIG. 3.

In order to maintain the integrity of the electrode material in the electrode constructions 11 and to minimize potential differences between electrode constructions, it is desirable to cover and bridge the Ag/AgCl coatings provided on the rounded ends 27. This is accomplished by the use of a flexible covering 56 which overlies the rounded ends 27 of the electrodes 11 and is draped into contact therewith. The covering 56 has a multilayer construction and has an outer layer 57. The outer layer 57 is a non-conductive or insulating layer and is formed of a suitable plastic or cloth. The outer layer 57 overlies an ionically conductive hydrogel layer or pad 58 which is in direct contact with the exposed surface of the rounded ends 27 of the electrodes 11. As can be seen, the covering 56 generally assumes the contours of the rounded ends and makes intimate contact with the rounded ends. The covering is provided with pull tab 61 which extends beyond the electrodes 11 and is adapted to be grasped by the hand so that the covering can be lifted off of the electrodes 11 when it is desired to utilize the same.

Figure 4:
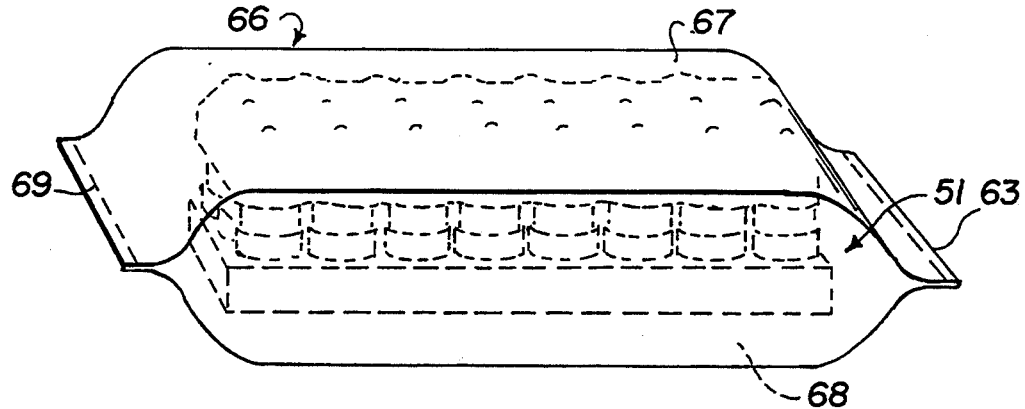
FIG. 4 is a isometric view showing an additional outer package utilized for enclosing the package shown in FIG. 3.

The holder or package 51 can be packaged in an additional hermetically sealed package, as for example a package 66 shown in FIG. 4 formed of two sheets 67 and 68 of a suitable packaging material such as a plastic material which are sealed along the edges 69 to provide a hermetically sealed package for shipping and storing the holder contained therein until it is ready to be used. Also the sheet 67 and 68 can be formed of a metallized polymer hermetically sealed to prevent water loss. When it is desired to use the same, the package can be opened by a scissors or other means to give access to the holder 51, after which the protective coating covering 56 on the holder can be removed to give access to the electrodes 11 therein. The electrodes 11 can then be utilized to make EEG measurements in the manner described in the co-pending application Ser. No. 07/790,412 filed on Nov. 8, 1991.

Similar packaging can be utilized for the electrodes 31 and consists of a holder or package 71 which is provided with a conductive tray 72 that has holes 73 therein arranged in the same manner as in the tray 52. A covering 76 of the same type as the covering 56 overlies the upper open ends of the electrodes 31 and is in contact therewith to seal and bridge the electrodes 31 until they are ready for use. The covering is provided with a pull tab 77 which is used for the same purpose as the pull tab 61. The holder 71 can then be hermetically packaged in the same manner as the holder 51.

In connection with the foregoing, it can be seen that there has been provided a new and improved electrode construction and packaging therefor. In the electrode 11 as shown in FIG. 1, the exposed surface of the rounded end serves as the reference element whereas in the electrode shown in FIG. 2, the reference element is in contact with conductor means and is buried within the gelled electrolyte. Thus in the embodiment of the electrode shown in FIG. 2, the gelled electrolyte merely forms an electrolytic bridge between the reference layer 47 and the skin of the patient engaged by the gelled electrolyte. This has an advantage in that the exposed surface 48 can be damaged without affecting the performance of the electrode.

Figure 5:
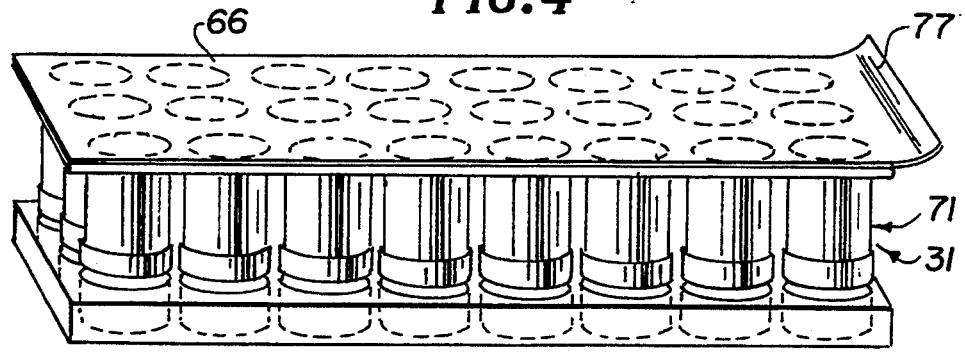
FIG. 5 is an isometric view of a package for the electrode construction shown in FIG. 2.

The packaging hereinbefore described and as shown in FIGS. 3 and 5 electrically and electrolytically interconnect all of the reference elements of the electrodes in each package. Thus, differences in reference potentials of the electrodes in any one package are minimized and remain so during storage before use. Thus, the reference potentials of the electrodes in a package are stable. The electrodes require no further conditioning and are ready to be used when removed from the package.

What is claimed is:

1. An electrode construction comprising a support structure, a conductive electrode material carried by the support structure and having a length and a width and having proximal and distal extremities, said support structure including a compliant sleeve having an open end and surrounding the distal extremity of the conductive electrode material while permitting the conductive electrode material to protrude through the open end and conductive contact means making contact with the proximal extremity of the conductive electrode material.

2. An electrode construction as in claim 1 wherein the length of the Conductive electrode material is at least approximately the same as the width of the conductive electrode material.

3. An electrode construction as in claim 1 wherein said electrode material is self supporting and has a blunt rounded end.

4. An electrode construction as in claim 1 wherein said support structure is in the form of a casing having a recess therein and wherein said conductive material is disposed in said recess in said casing and extends out of said casing.

5. An electrode construction as in claim 4 wherein said casing is at least partially conductive.

6. An electrode construction as in claim 1 wherein said support structure is at least partially conductive so that it can serve as an electrical coupling to the conductive material.

7. An electrode construction comprising a support structure, a conductive material carried by the support structure and having a length and a width said electrode construction having a length which is at least as great as its width, said support structure being in the form of a casing, including a compliant sleeve having a recess therein, said conductive material being disposed in said recess in said casing and extending out of said casing, said conductive material being formed of a gelled electrolyte and having a cohesive force which is greater than its adhesive force, said sleeve being formed of a material which serves as a moisture barrier.

8. An electrode construction as in claim 7 wherein said sleeve is formed of a compliant material.

9. An electrode construction as in claim 7 together with a reference element in contact with the conductive material.

10. An electrode construction as in claim 9 wherein said reference element is comprised of Ag/AgCl.

11. An electrode construction as in claim 8 wherein said reference element is in contact with the casing and said gelled electrolyte is in contact with the reference element.

12. An electrode construction as in claim 7 wherein said conductive material is in the form of a dry conductive elastomer having an exposed extremity and wherein said reference element is formed on the exposed extremity.

13. A package comprising holding means, a plurality of electrode constructions disposed in the holding means, each electrode construction having a conductive material and a reference element and means carried by the holding means for electrically and electrolytically bridging the reference elements of the electrode constructions to minimize potential differences between the reference elements and to ensure the reference potentials on reference elements are stable.

14. A package as in claim 13 together with an enclosure having moisture barrier properties for enclosing said holding means.

15. A package as in claim 13 wherein said means for electrically and electrolytically bridging the reference elements includes a conductive layer.

16. A package comprising holding means, a plurality of electrode constructions disposed in said holding means, each of said plurality of electrode constructions being comprised of a conductive casing having conductive material disposed therein and extending out of the casing and having an exposed surface, an ionically conductive pad overlying said exposed surfaces of said electrode constructions and being in contact therewith and a hermetically sealed container enclosing said holding means with said electrode constructions disposed therein with the overlying ionically conductive pad.

17. A package as in claim 16 wherein said ionically conductive pad is comprised of a conductive substrate having a surface and having a hydrogel disposed on the surface and having the hydrogel in contact with the exposed surface of the conductive material of the electrode constructions.

18. A package as in claim 16 wherein said pad is provided with a pull tab to facilitate removal of the pad from the electrode constructions.

* * * * *